(12) United States Patent
Tah et al.

(10) Patent No.: US 11,399,943 B2
(45) Date of Patent: Aug. 2, 2022

(54) FURLOW INSERTION DEVICE

(71) Applicant: Boston Scientific Scimed, Inc., Maple Grove, MN (US)

(72) Inventors: Richard C. Tah, Milford, MA (US); Brian P. Watschke, Minneapolis, MN (US); Matthew Lee Nelson, Plymouth, MN (US); John Christian Kulaga, Chicago, IL (US); Kyle Pickett, St. Louis, MO (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 711 days.

(21) Appl. No.: 16/357,851

(22) Filed: Mar. 19, 2019

(65) Prior Publication Data

US 2019/0290435 A1 Sep. 26, 2019

Related U.S. Application Data

(60) Provisional application No. 62/647,272, filed on Mar. 23, 2018.

(51) Int. Cl.
*A61F 2/26* (2006.01)
*A61B 17/34* (2006.01)
*A61B 90/00* (2016.01)
*A61B 17/04* (2006.01)

(52) U.S. Cl.
CPC ............ *A61F 2/26* (2013.01); *A61B 17/3468* (2013.01); *A61B 17/0469* (2013.01); *A61B 17/0483* (2013.01); *A61B 2017/3454* (2013.01); *A61B 2090/061* (2016.02); *A61B 2090/062* (2016.02); *A61B 2090/0807* (2016.02)

(58) Field of Classification Search
CPC .............................. A61F 2/26; A61B 17/3468
See application file for complete search history.

(56) References Cited

U.S. PATENT DOCUMENTS

| 5,628,757 A | 5/1997 | Hasson |
| 2004/0167574 A1 | 8/2004 | Kuyava et al. |
| 2010/0160722 A1 | 6/2010 | Kuyava et al. |

OTHER PUBLICATIONS

International Search Report and Written Opinion for International Application No. PCT/US2019/023118, dated Jul. 8, 2019, 16 pages.
"AMS 700® Penile Prosthesis Operating Room Manual", American Medical Systems, Inc., 2012, 36 pages.

*Primary Examiner* — John P Lacyk
(74) *Attorney, Agent, or Firm* — Brake Hughes Bellermann LLP

(57) ABSTRACT

According to a general aspect, an insertion device can include an elongate barrel having an opening defined in a distal end; a lumen defined within the elongate barrel, the lumen being accessible through the opening; and an obturator disposed within the lumen of the elongate barrel. The obturator can be movable within the lumen between a proximal position in the elongate barrel and a distal position in the elongate barrel. The obturator, in its distal position in the elongate barrel, can be configured to receive a needle via the opening. The obturator, in its proximal position in the elongate barrel, can be configured to secure the needle within the elongate barrel.

20 Claims, 11 Drawing Sheets

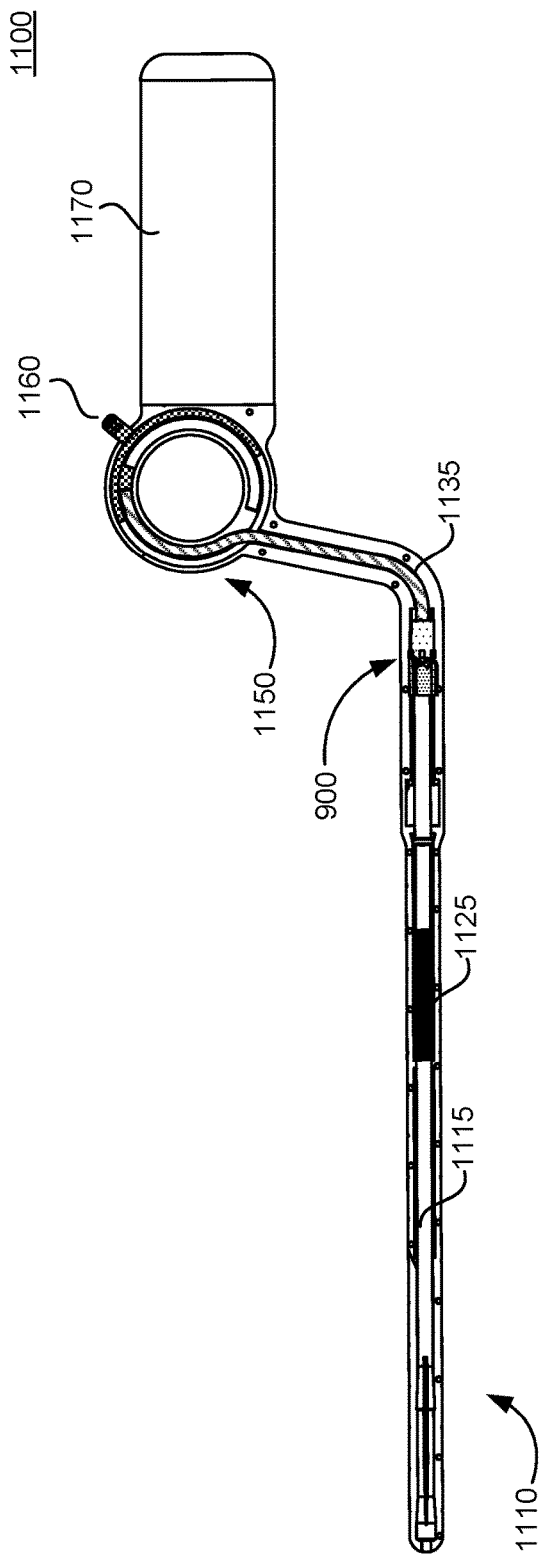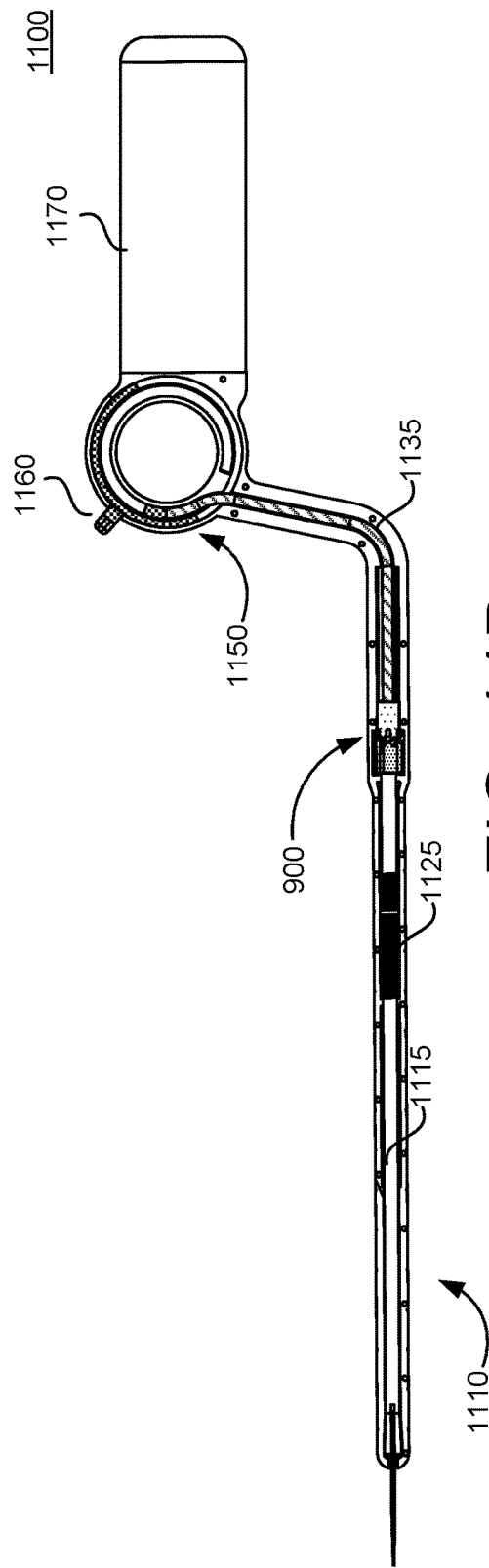
FIG. 11A
FIG. 11B

FURLOW INSERTION DEVICE

CROSS-REFERENCE TO RELATED APPLICATION

This application is a Nonprovisional of, and claims priority to, U.S. Patent Application No. 62/647,272, filed on Mar. 23, 2018, entitled "FURLOW INSERTION DEVICE", which is incorporated by reference herein in its entirety.

TECHNICAL FIELD

This disclosure relates generally to devices for insertion of bodily implants and, more specifically, to insertion devices for bodily implants, such as penile prostheses.

BACKGROUND

One treatment for chronic, organic, male erectile dysfunction is the implantation of a penile prosthesis that mechanically erects the penis. Such prostheses can have different physical constructions (e.g., materials, mechanical structure and function, etc.) and configurations (e.g., physical dimensions, etc.). For instance, such a penile prosthesis can be in the form of a cylinder (e.g., malleable, inflatable, etc.) that is selected based on the physical requirements of an intended recipient (a patient). For instance, an appropriate penile prosthesis can be implanted within a corpus cavernosum (corpus cavernosa) of a patient's penis by medical personnel that are trained and knowledgeable regarding the implantation and use of penile prostheses.

Insertion devices (e.g., furlow insertion devices) can be used to facilitate the insertion of a penile prosthesis into the corpus cavernosum of a patient. Such furlow insertion devices can be used for measurement of an insertion length within the corpus cavernosum, as well as for facilitating insertion of a penile prosthesis by deploying a suture-carrying needle, where the needle and/or suture are used to introduce (draw, pull, insert, implant, etc.) the prosthesis into the corpus cavernosum.

In some existing devices, a needle (e.g., which can be referred to as a Keith needle) used in the insertion of a penile prosthesis can be, at least partially, prematurely deployed from (e.g., come out of, fall out of, etc.) a corresponding insertion device, which can result in a tip of the needle piercing (e.g., damaging, injuring, etc.) the corpus cavernosum before the insertion device is fully inserted to the intended position for deploying the needle (e.g., through a glans of the penis). Also in some existing devices, improper measurement of insertion depth (e.g., for selecting a properly sized prosthesis) can occur due to occlusion of the insertion device (e.g., by blood, etc.) when it is inserted into a body of a patient. Such improper measurement can result in selection of an improperly sized prosthesis for a patient. Further, for some existing devices, accessibility to an insertion point for the insertion device can be compromised in some instances. For instance, in procedures being performed on heavy-set patients, body mass of the patient can inhibit (interfere with, etc.) medical personnel's access to an insertion point (e.g., an incision site) for the insertion device. Still further in some existing devices, furlow insertion devices are sterilized after each use, and then reused in subsequent patient procedures. It can, however, be difficult to clean and sterilize such devices due to, at least, a slot in the insertion device that can be used for threading sutures along a length of the device and/or an interior of the insertion device, where incomplete or inadequate sterilization could lead to patient infections.

SUMMARY

In a general aspect, an insertion device can include an elongate barrel, where a distal end of the elongate barrel has an opening defined therein. The insertion device can also include a lumen defined within the elongate barrel, the lumen being accessible through the opening. The insertion device can further include an obturator disposed within the lumen of the elongate barrel. The obturator can be movable within the lumen between a proximal position in the elongate barrel and a distal position in the elongate barrel. The obturator, in its distal position in the elongate barrel, can be configured to receive a needle via the opening. The obturator, in its proximal position in the elongate barrel, can be configured to secure the needle within the elongate barrel.

Implementations can include one or more of the following features. For example, in some implementations, the obturator can include a collet disposed at a distal end of the obturator. The collet can have a plurality of tags. The plurality of tags can be biased to receive the needle when the obturator is in its distal position in the elongate barrel. The plurality of tags can be compressed to secure the needle when the obturator is in its proximal position in the elongate barrel.

In some implementations, the lumen of the elongate barrel can include a flared portion disposed at the distal end of the elongate barrel. The flared portion can be configured to allow the plurality of tags to bias to receive the needle when the collet is disposed within the flared portion. The lumen of the elongate barrel can include a cylindrical portion disposed proximal to the flared portion. The cylindrical portion can be configured to compress the plurality of tags when the collet is disposed within the cylindrical portion. A diameter of the flared portion of the lumen can be greater than a diameter of the cylindrical portion of the lumen.

In some implementations, the insertion device can include a biasing spring that can be axially disposed around at least a portion of the obturator and disposed within the lumen of the elongate barrel. The biasing spring can be configured to bias the obturator in its proximal position.

In some implementations, the insertion device can include a measurement scale disposed on an exterior surface of the elongate barrel and a measurement ring that is slidable along the elongate barrel to indicate an insertion depth of the elongate barrel. The elongate barrel can include a groove or a slot that is defined therein. The groove or slot can extend along the elongate barrel. The measurement ring can be slidable along the groove or the slot. The measurement scale can be inscribed on an exterior surface of the elongate barrel.

In some implementations, the elongate barrel can be aligned along a first longitudinal axis, and the insertion device can include a housing disposed at a proximal end of the elongate barrel. The housing can include an elbow portion coupled with the elongate barrel and a straight portion coupled with the elbow portion. The straight portion can be aligned along a second longitudinal axis. The second longitudinal axis can define an angle with the first longitudinal axis. The angle can be between ninety degrees and one-hundred-eighty degrees.

In some implementations, the housing can have a lumen disposed therethrough. The insertion device can include an actuator disposed at a distal end of the housing and a flexible connecting rod having a first portion disposed within the lumen of the housing and a second portion disposed within the lumen of the elongate barrel. The flexible connecting rod can be disposed between the actuator and the obturator. The actuator and the flexible connecting rod can be configured, in response to movement of the actuator by a user, to move the obturator from its proximal position to its distal position.

In some implementations, the insertion device can include a handle coupled with the housing. The handle can be aligned along a third longitudinal axis The third longitudinal axis can be parallel with, non-parallel with, and/or offset from the first longitudinal axis.

In some implementations, the insertion device can include a housing disposed at a proximal end of the elongate barrel and coupled with the elongate barrel, where the housing has a lumen disposed therethrough. The insertion device can include an actuator disposed at a distal end of the housing and a connecting rod having a first portion disposed within the lumen of the housing and a second portion disposed with the lumen of the elongate barrel. The connecting rod can be disposed between the actuator and the obturator. The actuator and the connecting rod can be configured, in response to movement of the actuator by a user, to move the obturator from its proximal position to its distal position. The connecting rod can be a flexible connecting rod. The actuator can include at least one of a plunger, a squeeze lever, or a rotating knob disposed in the housing.

In some implementations, the insertion device can include a locking mechanism that is configured to selectively lock the obturator in its distal position.

In some implementations, the insertion device can include an indexing mechanism configured to, in response to actuation of the insertion device, alternate between a first fixed position and a second fixed position. When the indexing mechanism is in its first fixed position, the obturator can be fixed in its distal position in the elongate barrel. When the indexing mechanism is in its second fixed position, the obturator can be fixed in its proximal position in the elongate barrel.

In another general aspect, a method for inserting a penile prosthesis can include making a penoscrotal or an infrapubic incision in a body of a patient, capturing a needle in an obturator of an insertion device to secure the needle within an elongate barrel of the insertion device and pulling a suture inserted in an eye of the needle into a slot in the elongate barrel. The method can also include, using a handle of an insertion device to manipulate the insertion device to perform an insertion of the elongate barrel, via the incision, into a corpus cavernosum of a penis of the patient. The method can further include attaching a penile prosthesis to the suture and actuating the insertion device to deploy at least a portion of the needle through a glans of the penis. The method can still further include withdrawing the elongate barrel from the corpus cavernosum and the incision, and implanting the penile prosthesis in the corpus cavernosum by pulling the prosthesis through the incision and into to the corpus cavernosum by pulling the needle and suture through the glans.

Implementations can include one or more of the following features. For example, in some implementations, capturing the needle in the obturator can include capturing the needle with tags of a collet disposed at a distal end of the obturator.

In some implementations, the insertion of the elongate barrel can be a second insertion, and the method can include, prior to performing the second insertion, using the handle of the insertion device, manipulating the insertion device to, via the incision, perform a first insertion of the elongate barrel of the insertion device into the corpus cavernosum. The method can include sliding a ring disposed on the barrel proximate the incision, withdrawing the elongate barrel from the corpus cavernosum and the incision, and determining, based on a measurement scale inscribed on the elongate barrel and position of the ring on the elongate barrel, a depth of insertion of the elongate barrel in the corpus cavernosum. The penile prosthesis can be selected based on the depth of insertion. Sliding the ring can include sliding the ring along a groove in the elongate barrel or the slot in the elongate barrel.

BRIEF DESCRIPTION OF THE DRAWINGS

FIGS. 11A and 11B are cross-sectional views of yet another furlow insertion device according to an embodiment.

DETAILED DESCRIPTION

Figure 1A:
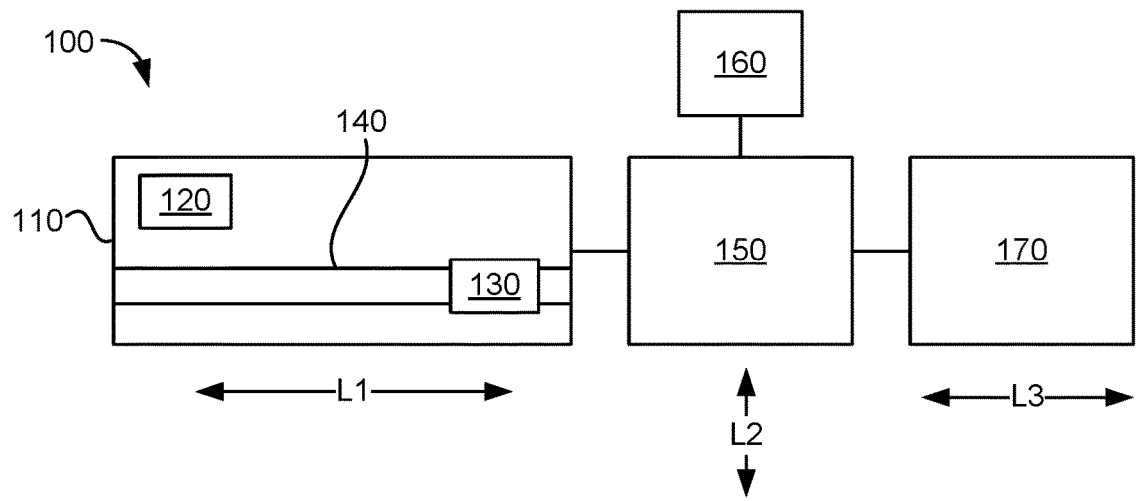
FIGS. 1A, 1B and 1C schematically illustrate a furlow insertion device that can be used for insertion of a penile prosthesis according to an embodiment.

Detailed embodiments are disclosed herein. However, it is understood that the disclosed embodiments are merely examples, which may be embodied in various forms. Therefore, specific structural and functional details disclosed herein are not to be interpreted as limiting, but merely as a basis for the claims and as a representative basis for teaching one skilled in the art to variously employ the embodiments in virtually any appropriately detailed structure. Further, the terms and phrases used herein are not intended to be limiting, but to provide an understandable description of the present disclosure.

The terms "a" or "an," as used herein, are defined as one or more than one. The term "another," as used herein, is defined as at least a second or more. The terms "including"

and/or "having", as used herein, are defined as comprising (i.e., open transition). The term "coupled" or "moveably coupled," as used herein, is defined as connected, although not necessarily directly and mechanically.

In general, the embodiments are directed to medical devices such as insertion devices for penile prostheses or other bodily implants. The term patient may hereafter be used for a person who benefits from the medical device or the methods disclosed in the present disclosure. For example, the patient can be a person whose body is implanted using the medical device or benefits from the methods disclosed for operating the medical devices of the present disclosure. For example, in some embodiments, the patient may be a human male, a human female, or any other mammal.

The terms proximal and distal described in relation to various devices, apparatuses, and components as discussed in the subsequent text of the present disclosure are referred to using a point of reference. The point of reference, as used in this description, is a perspective of a person who uses the disclosed insertion devices to implant a bodily implant, such as a penile prosthesis. The person may be a surgeon, a physician, a nurse, a doctor, a technician, and the like who may perform the implantation procedure. The term proximal refers to an area or portion that is closer or closest to the person during the implantation procedure. The term distal refers to an area or portion that is farther from, or farthest from the person.

The embodiments discussed herein may provide improvements to penile prosthesis insertion devices (e.g., furlow insertion devices, furlow insertion tools, insertion tools, devices, tools, etc.). For example, such insertion devices can be configured to self-load and secure a needle in a barrel of the insertion device, which can prevent premature deployment of the needle (e.g., prevent the needle from inadvertently coming out of the tool).

Further, in some embodiments, such insertion devices can be produced using low-cost bio-compatible materials, such as bio-compatible plastics, or otherwise, as compared with tools constructed using primarily surgical grade metals, for example. Accordingly, in certain embodiments, an insertion device such, as those described herein, can be cost-effective as a single-use device, where the insertion device can be provided in sterile packaging and then disposed of after use in performing a single implantation procedure on a patient, which can reduce the risk of patient infection from reuse and eliminate the need for sterilization of the insertion device.

In some embodiments, a furlow insertion device can be ergonomically arranged to facilitate easier access to an implantation site (e.g., incision site) for some patients, such as heavy-set patients by allowing for manipulation of the device at a distance that is farther away from the patient's body than in some current insertion devices. Also, in certain embodiments, an insertion device can include a locking mechanism that facilitates ease of loading of a needle (e.g., a Keith needle) and suture in the insertion device.

Figure 1B:
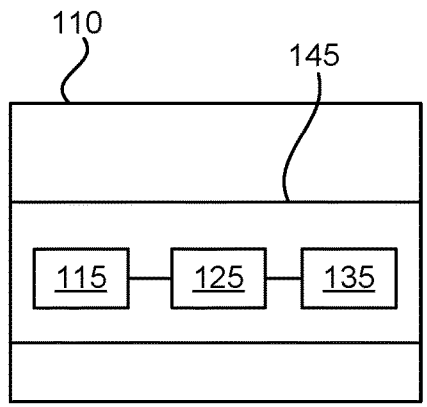
Figure 1C:
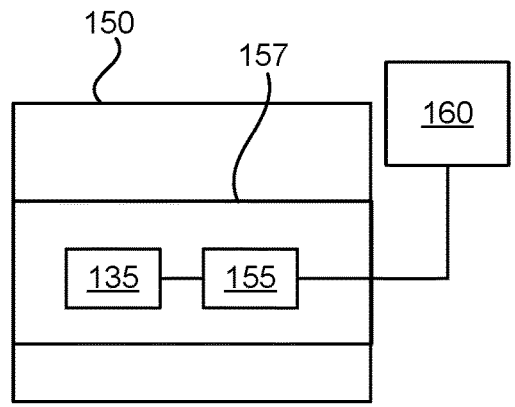
Figure 1D:
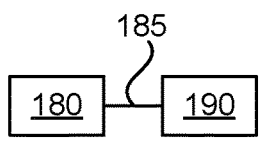
FIG. 1D schematically illustrates a needle, a suture and a penile prosthesis according to an embodiment.

FIGS. 1A, 1B and 1C schematically illustrate a furlow insertion device (device) 100 that can be used for insertion (implantation, etc.) of a penile prosthesis in a penis of a patient according to an embodiment. FIG. 1D schematically illustrates a needle 180, a suture 185 and a penile prosthesis 190 that can be used in conjunction with the insertion tool 100 according to an embodiment. In some implementations, the needle 180, the suture 185 and the penile prosthesis 190 can be used in conjunction with other insertion tools, such as those described herein.

As shown in FIG. 1A, the device 100 can include an elongate barrel 110 that is aligned (arranged, situated, etc.) along a longitudinal axis L1. The elongate barrel 110 can have a measurement scale 120 that is disposed on an outer surface of the elongate barrel 110. In certain implementations, the measurement scale 120 can be inscribed, printed, engraved, etc. on the outer surface of the elongate barrel 110. The elongate barrel 110 can also include a measurement indicator 130. In certain implementations, the measurement indicator 130 can be a measurement ring that is axially disposed around the elongate barrel 110. The measurement indicator 130 can slide along the elongate barrel 110 (along the axis L1) in a groove or slot 140 (referred to hereafter as slot 140) that is included in the elongate barrel 110. In some implementations, the slot 140 can also be used to receive a suture that is attached to (threaded in) a needle that can be inserted in the elongate barrel 110 of the device 100, such as described herein. The measurement indicator 130 can be used, in conjunction with the measurement scale 120, to determine an insertion depth of the elongate barrel 110, e.g., when the elongate barrel 110 is inserted in a corpus cavernosum of a patient. This insertion depth can be used to select an appropriately sized penile prosthesis for implantation in the patient.

The device 100 can also include a housing 150 that is coupled with the elongate barrel 110. In some implementations, the elongate barrel 110 and the housing 150 can be included in a unitary (monolithic) structure. In other implementations, the elongate barrel 110 and the housing 150 can be separate structures that are coupled (attached, etc.) to each other, such as using an adhesive, being press-fit together, welded together, and so forth. As shown in FIG. 1A, the housing 150 can have at least a portion that is aligned along a second longitudinal axis L2. The axis L1 of the elongate barrel 110 and the axis L2 of the housing 150 can define (form, etc.) an angle. In some implementations, the angle defined by the axis L1 and the axis L2 can be between ninety degrees and one-hundred-eighty degrees.

The device 100 also includes an actuator 160 that is coupled (operationally coupled, etc.) with the housing 150. The actuator 160 can, depending on the particular implementation, take a number of forms, such as those described herein. In some implementations, the actuator 160 can be used to operate the device 100 during the implantation of a penile prosthesis (e.g., to configure and/or operate the device 100 for loading, capturing and deploying a needle, such as a Keith needle, used for penile prosthesis implantation).

As illustrated in FIG. 1A, the device 100 can also include a handle 170 that is coupled with the housing 150. The handle 170 can be aligned along a third longitudinal axis L3. In some implementations, the axis L3 of the handle 170 can be parallel with the axis L1 of the elongate barrel 110. In other implementations, the axis L3 of the handle 170 can be non-parallel or offset with respect to the axis L1 of the elongate barrel 110. The arrangement of the elongate barrel 110, the housing 150 and/or the handle 170 in the device 100 can, as was noted above, facilitate easier access to an implantation site (e.g., an incision site) for some patients, such as heavy-set patients, by allowing for manipulation of the device 100 at a distance away from the patient's body, which can prevent interference by body mass of the patient when a user is attempting to utilize the device 100 during the procedure for implantation of a penile prosthesis.

FIG. 1B schematically illustrates further aspects (elements) of the elongate barrel 110 of the device 100 shown in FIG. 1A according to an embodiment. In some implementations, the elements shown in FIG. 1B can be implemented and/or included within the elongate barrel 110 of the insertion device 100. As illustrated in FIG. 1B, the elongate barrel 110 can include an obturator 115, a biasing spring 125 and a connecting rod 135, which can be disposed within a lumen 145 that is defined in the elongate barrel 110. The lumen 145 can extend along the axis L1 of the elongate barrel and can extend from a distal end of the elongate barrel 110 to a proximal end of the elongate barrel 110 (e.g., can be a through-lumen extending the length of the elongate barrel 110).

The obturator 115 can be configured to, based on operation of the device 100 using the actuator 160, receive, capture and deploy a needle for implanting a penile prosthesis. The biasing spring 125 can be axially disposed around the obturator 115 (or can be disposed between the obturator 115 and the connecting rod 135). The biasing spring 125 can apply a force to the obturator 115 and/or the connecting rod 135 to bias the obturator 115 to a fixed position within the lumen 145 of the elongate barrel. For instance, in some implementations, the biasing spring 125 can bias the obturator 115 to a fixed proximal position in the lumen 145. The obturator 115 can be configured, when in its fixed proximal position to retain (hold, secure, etc.) a needle within the lumen 145, and can prevent the needle from being prematurely deployed from (e.g., exiting) the elongate barrel 110 during the implantation of a penile prosthesis.

The actuator 160, when manipulated by a user, can cause the obturator 115 (along with the connecting rob 135) to move distally along the axis L1, from its proximal position to a distal position in the lumen 145 while compressing the biasing spring 125. In some implementations, a locking mechanism can be included that can secure (lock) the obturator 115 in its distal position (e.g., after a user releases the actuator 160), preventing the compressed biasing spring 125 from decompressing and biasing the obturator 115 back to its fixed proximal position. The obturator 115 can be configured, when in its distal position (fixed or non-fixed) to receive a needle to be secured by the obturator in its proximal position within the lumen 145, and to deploy the needle (e.g., through a glans of a patient's penis) during a process for implanting a penile prosthesis.

FIG. 1C schematically illustrates aspects (elements) of the housing 150 of the device 100 shown in FIG. 1A according to an embodiment. In some implementations, the elements shown in FIG. 1C can be implemented and/or included within the housing 150 of the insertion device 100. As illustrated in FIG. 1C, the housing 150 can include at least a portion of the connecting rod 135. For instance, in some implementations, a first portion of the connecting rod 135 can be disposed within the elongate barrel 110 and a second portion of the connecting rod 135 can be disposed within the housing 150.

As shown in FIG. 1C, the housing 150 can also include a locking mechanism 155. In some implementations, the locking mechanism 155 could, alternatively, be included in the elongate barrel 110. The locking mechanism 155 can be an indexing mechanism (such as the mechanism described with respect to FIGS. 6A-6B, 7A-7C, 8A-8B and 9A-9C). For instance, the locking mechanism 155, in response to actuation of the device 100 with the actuator 160, can alternate between a first position and a second position, which can be a first fixed position and a second fixed position. In the first fixed position, the locking mechanism 155, the biasing spring 125 and/or the connecting rod 135 can cause the obturator 115 to be fixed (locked) in its proximal (needle securing) position. In the second fixed position, the locking mechanism 155, the biasing spring 125 and/or the connecting rod 135 can cause the obturator 115 to be fixed (locked) in its distal (needle receiving and deploying) position.

In the housing 150 shown in FIG. 1C, the connecting rod 135 and the locking mechanism 155 can be disposed within a lumen 157 that is defined in the housing 155. The lumen 157, which can be coaxial with the lumen 145 of the elongate barrel, can extend from a distal end of the housing 150 to a proximal end of the housing 150 (e.g., can be a through-lumen). In certain implementations, the actuator 160 can be disposed at the proximal end of the housing 150 and can, when manipulated by a user, affect movement of the obturator 115 along the axis L1 in the elongate barrel 100 (e.g., distal movement) by applying a force to the connecting rod 135 that is communicated to the obturator 115 (via movement of the connecting rod in the lumen 157 and/or the lumen 145), such that the biasing spring 125 is compressed, and the obturator 115 moves distally in the lumen 145.

Figure 12:
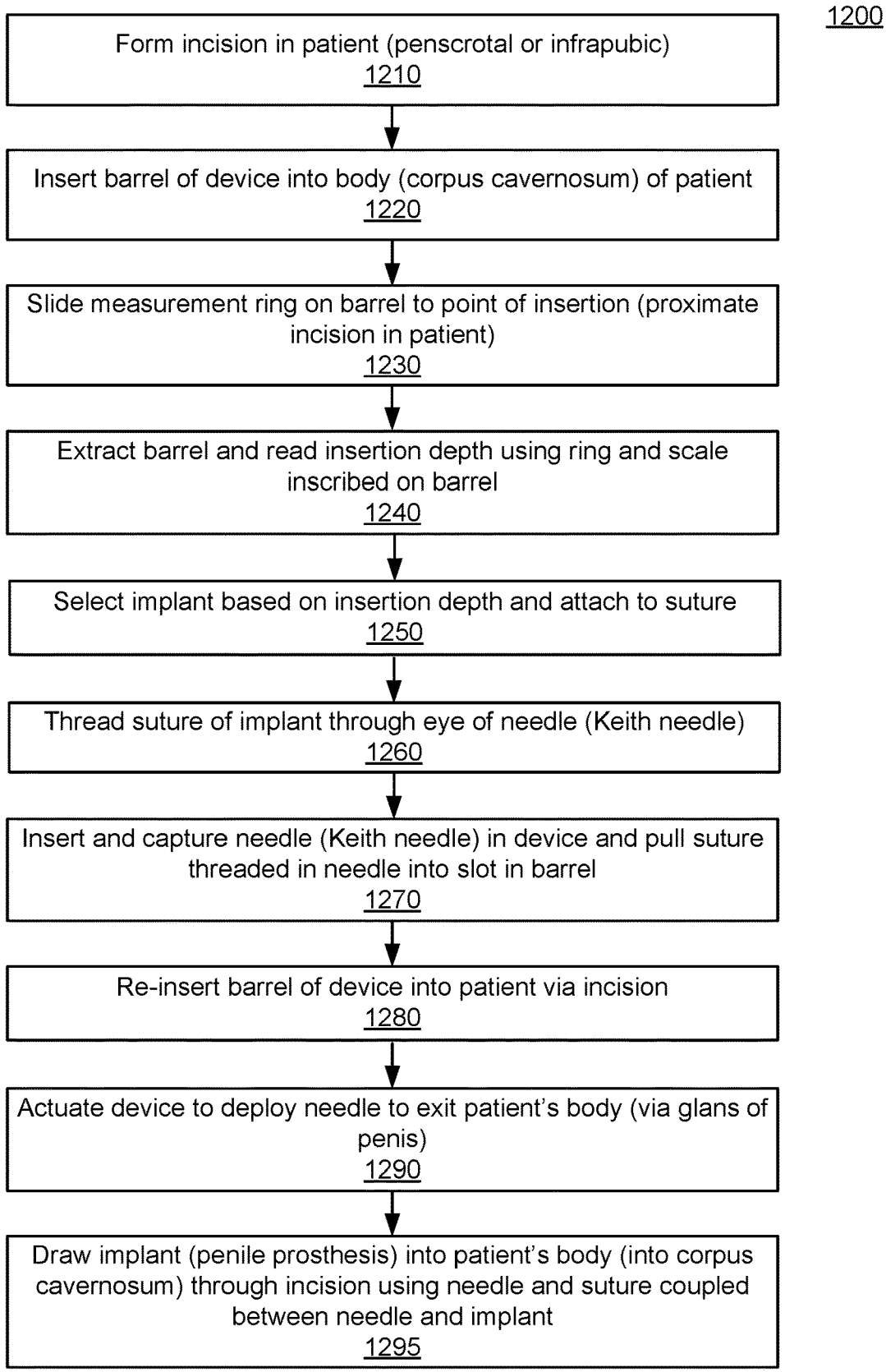
FIG. 12 is a flowchart of a method for inserting a penile prosthesis according to an embodiment.

The needle 180 (e.g., a Keith needle), the suture 185 and the penile prosthesis of FIG. 1D can be used in conjunction with the device 100, or other insertion devices, such as those disclosed herein, for implanting the penile prosthesis 190 in a corpus cavernosum of a patient's penis. An example method for performing such an implantation is illustrated in FIG. 12 and described below.

Figure 2:
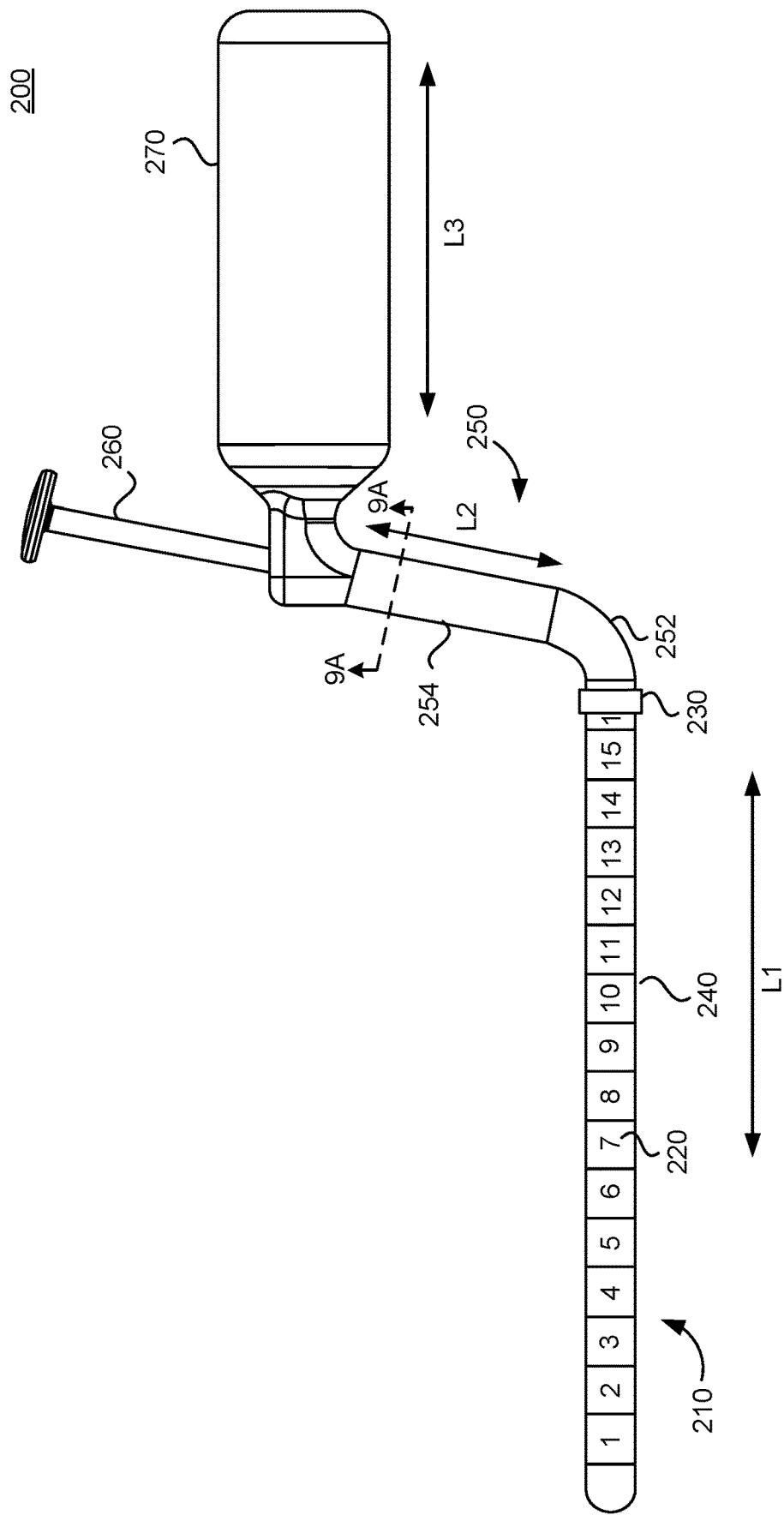
FIG. 2 illustrates a furlow insertion device that can be used for insertion of a penile prosthesis according to another embodiment.

FIG. 2 illustrates a furlow insertion device (device) 200 that can be used for insertion of a penile prosthesis according to another embodiment. The device 200 can, however, implement the device 100 of FIG. 1. As shown in FIG. 2, the device 200 includes an elongate barrel 210, a measurement indicator (measurement ring 230), an actuator 260, a housing 250 that is coupled with (or integrated monolithically with) the elongate barrel 210, and a handle 270. A section line 9A-9A is also shown in FIG. 2, which illustrates a cut line through the housing corresponding with the cross-sectional view illustrated in FIG. 9A.

As shown in FIG. 2, the elongate barrel 210 can include a measurement scale 220 that is disposed on an outer surface of the elongate barrel 210. Depending on the implementation, the measurement scale 210 can be inscribed, printed, engraved, etc. on the elongate barrel 210. The elongate barrel 210 can also include a slot (or groove) 240 that is disposed along an underside of the elongate barrel 210 and, therefore, not explicitly shown in FIG. 2. In the insertion device 200, the measurement ring 230 can slide along the slot 240. For instance, the measurement ring 230, after inserting the elongate barrel 210 into the body of a patient (e.g., to a depth of a corpus cavernosum), can be slid, guided by the slot 240, along the elongate barrel 210, until the measurement ring 230 is proximate with an insertion site for the elongate barrel 210. After extracting the elongate barrel 210 from the patient, the position of the measurement ring 230 on the measurement scale 220 can be used to determine the insertion depth. Further, a suture, such as the suture 185 of FIG. 1D, can be pulled into the slot 240 when performing an implantation process using the device 200, such as in accordance with the method 1200 illustrated in FIG. 12.

In the device 200, the housing 250 includes a curved portion 252 that curves away from a central axis of the elongate barrel 210, the central axis of the elongate barrel being arranged along the axis L1. The housing 250 also includes a straight portion 254 that extends along the axis L2, where the axis L1 of the elongate barrel 210 and the axis L2 of the straight portion 254 define an angle between ninety degrees and one-hundred-eighty degrees. In certain implementations, a locking mechanism can be included in the device 200, e.g., in the elongate barrel 210 or in the housing 250, such as in the straight portion 254 of the housing 250.

An example locking mechanism that can be included in the device 200 is illustrated below in FIGS. 6A-6B, 7A-7C, 8A-8B and 9A-9C. The locking mechanism can be, for instance, an indexing locking mechanism.

The device 200 of FIG. 2 can further include an actuator 260, which is implemented as a plunger in the device 200. A user can operate (actuate) the device 200 by depressing the actuator 260 with his or her thumb, while holding the device 200 by the handle 270, the handle 270 being coupled with the housing 250. As shown in FIG. 2, the handle 270 can be arranged along the axis L3. Depending on the implementation, the axis L3 of the handle 270 can be parallel with, or non-parallel with the axis L1 of the elongate barrel 210.

Figure 3:
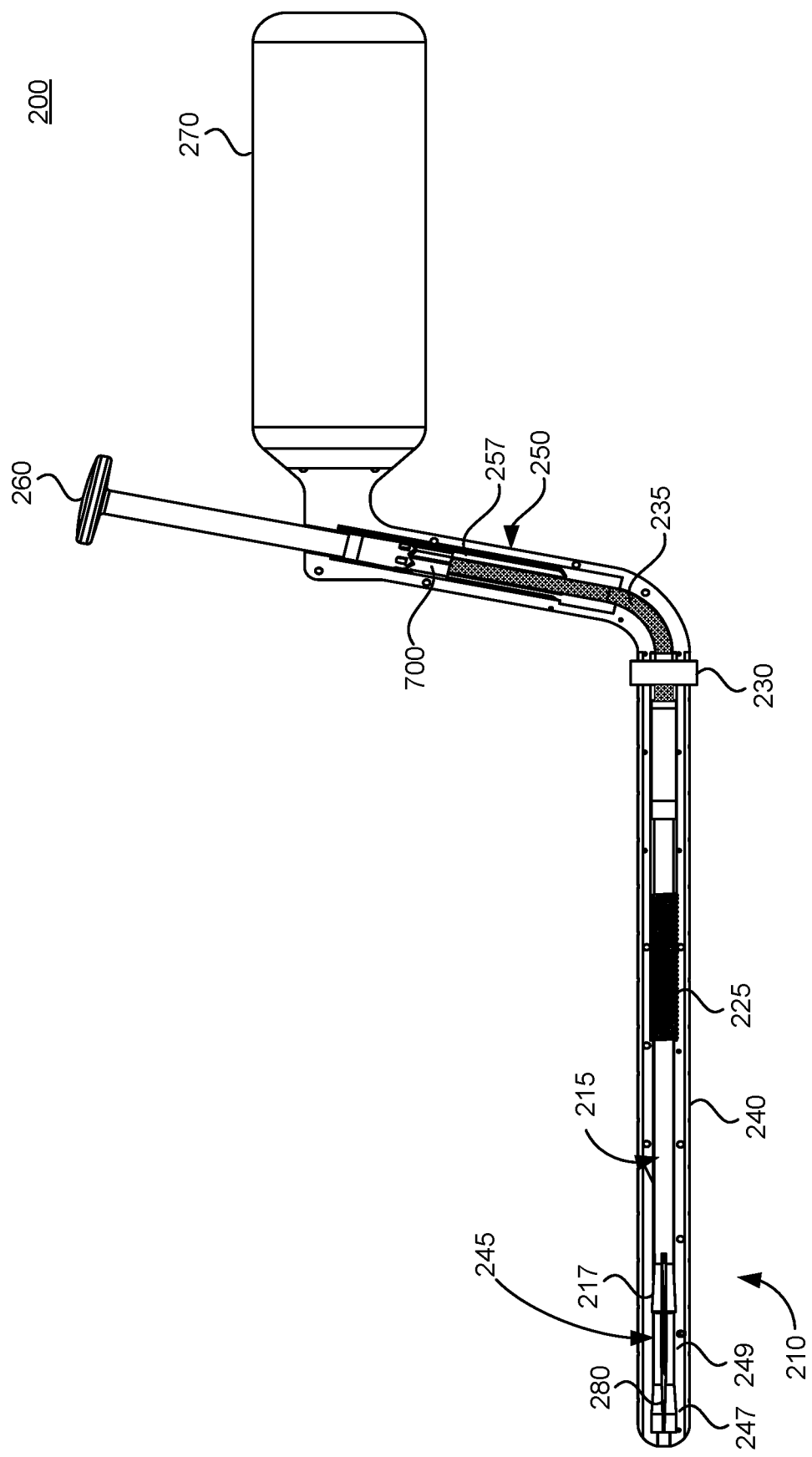
FIG. 3 illustrates a cross-sectional view of the furlow insertion device of FIG. 2 according to an embodiment.

FIG. 3 illustrates a cross-sectional view of the furlow insertion device 200 of FIG. 2 according to an embodiment. In FIG. 3, the elongate barrel 210 and the housing are shown in cross-section, to illustrated elements of the device 200 that can be disposed within the elongate barrel 210 and the housing 250, such as the elements of the device 100 illustrated in FIGS. 1B and 1C and described above.

As shown in FIG. 3, the device 200 can include an obturator 215 and a biasing spring 225 that are disposed within a lumen 245 that is defined within the elongate barrel 210. The biasing spring 225 can be axially disposed around the obturator and can contact one or more surfaces within the lumen 245 and/or engage with the obturator 215 to bias the obturator 215 in a proximal position, such as is illustrated in FIG. 3. The device 200 can also include a connecting rod 235, which can be a resilient, flexible connecting rod that has a first portion disposed within the lumen 245 of the elongate barrel and a second portion that is disposed within a lumen 257 of the housing 250.

As illustrated in FIG. 3, the connecting rod 235 can be disposed between the actuator 260 and the obturator 215. In the device 200, depressing the actuator 260 into the lumen 257 of the housing 250 will apply a force on the connecting rod 235 and that force will be communicate to the obturator 215 to move the obturator to a distal position in the lumen 245 of the elongate barrel 210. The force on the connecting rod and the obturator 215 can also compress the biasing spring 225. In certain implementations, a locking mechanism can be indexed in response to the actuator 260 being depressed and lock (fix) the obturator 215 in its distal position, with the biasing spring compressed. In such implementations, on a next depression of the actuator 260, the locking mechanism can index again and allow the biasing spring 225 to decompress and return the obturator 215 to its proximal position, such as shown in FIG. 3.

In certain implementations, the device 200 may not include a locking mechanism. In such devices, the obturator 215 can be maintained in its distal position by maintaining pressure on the actuator 260, or keeping the actuator 260 depressed. Releasing the actuator 260, or removing pressure from the actuator 260 in such implementations can allow the biasing spring 225 to decompress and move the obturator 215 from its distal position to it proximal position.

As also shown in FIG. 3, the obturator 215 can include a collet 217 disposed at a distal end of the obturator, where the collet 217 is configured to receive a needle 280 (which can be, e.g., a Keith needle) when the obturator 215 is in its distal position, and configured to secure (hold, retain, etc.) the needle in the collet 217 within the elongate barrel 210 when the obturator 215 is in its proximal position. As shown in FIG. 3, the lumen 245 of the elongate barrel 210 can included a flared portion at a distal end of the elongate barrel 210 and a cylindrical portion 249 that is disposed proximally of the flared portion 247 in the elongate barrel. The flared portion 247 and the cylindrical portion 249 of the lumen 245 can operate, in conjunction with collet 217, to allow the collet 217, based on a position of the obturator 215 in the lumen 245, to allow the collet 217 to open to receive or deploy the needle 280, or to close to retain the needle 280 in the collet 217. An example implementation of the collet 217 is illustrated in FIG. 4, while an example implementation of the flared portion 247 and the cylindrical portion 249 of the lumen 245, along with the collet 217, is illustrated in FIG. 5.

Figure 4:
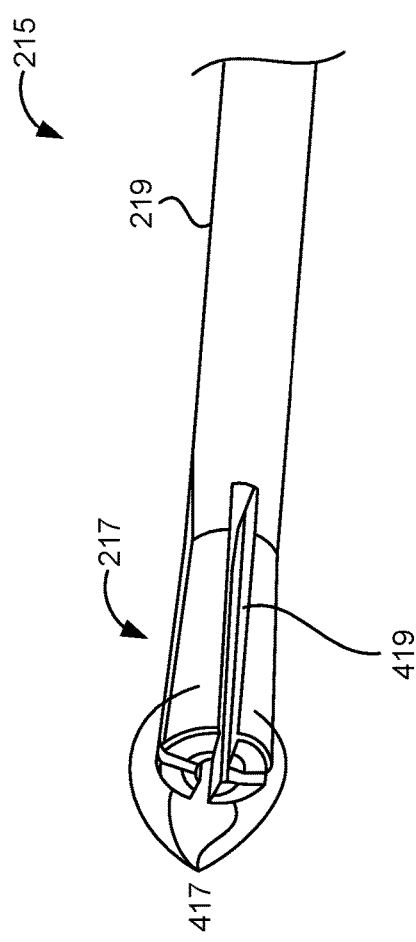
FIG. 4 illustrates a collet that can be included in a furlow insertion device according to an embodiment.

FIG. 4 illustrates an example implementation of the collet 217 of the device 200 of FIGS. 2 and 3 according to an embodiment. As discussed above, the collet 217 can be disposed at a distal end of the obturator 215 in the device 200. In some implementations, the collet 217 can include a plurality of tags that can be defined by forming splices 419 in the distal end of the obturator 215, where a diameter of the collet 217 is greater than a diameter of a shaft 219 of the obturator 215. The splices 419 can create an opening in the collet 217, e.g., between the tags 417, that is sized to receive the needle 280. As shown in FIG. 4, the tags 417 of the collet 217 can be radially disposed around the distal end of the obturator. Depending on the implementation, the collet 217 can include, for example, two to six tags.

Figure 5:
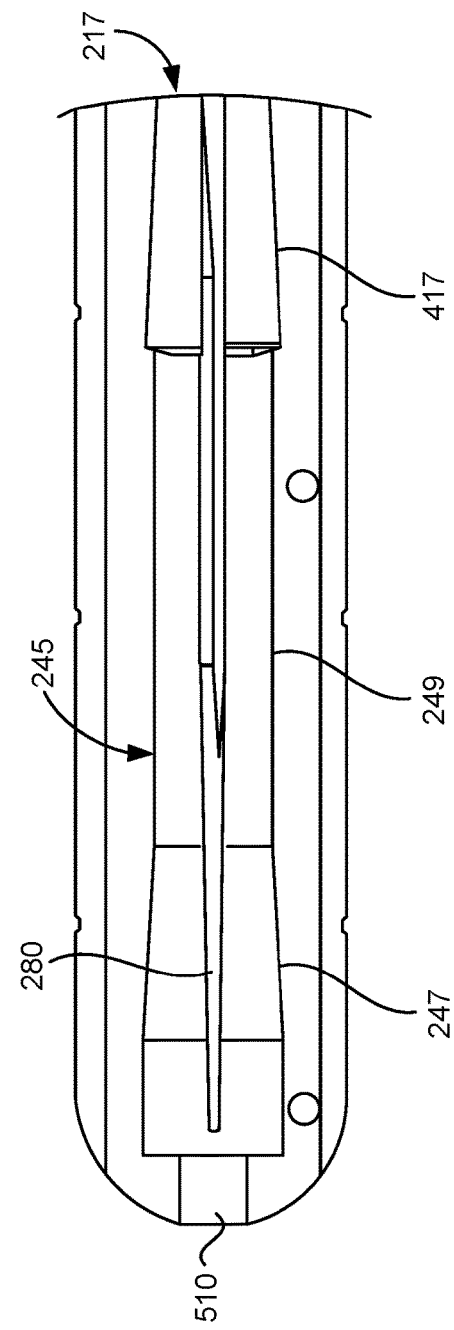
FIG. 5 is a partial cross-sectional view of a furlow insertion device illustrating a needle secured within the collet of FIG. 4 according to an embodiment.

FIG. 5 is a partial cross-sectional view of the device 200, illustrating the needle 280 secured within the collet 217 of FIG. 4 according to an embodiment. That is, FIG. 5 illustrates a cross-sectional view of a distal end of the device 200, as shown in FIG. 3, for example.

As shown in FIG. 5, the collet 217 and the needle 280 are disposed within the cylindrical portion 249 of the lumen 245 of the device 200. As can be seen in FIG. 5, the cylindrical portion 249 of the lumen 245 can have a diameter that is smaller than a diameter of the flared portion 247 of the lumen 245. The diameter of the cylindrical portion 245 can also be smaller than a diameter of the collet 217. Therefore, when the obturator 215 is located, e.g., biased by the biasing spring 224, in a position within the lumen 245 of the elongate barrel 210 such that the collet 217 is within the cylindrical portion 249, walls of the cylindrical portion 249 will apply inward pressure on the tags 417. This inward pressure on the tags 417 can cause the tags 417 to tighten on the needle 280, such that the needle 280 is secured within the collet 217 by the tags 417. In other words, in this arrangement, the needle 280 can be securely held within the elongate barrel 210 of the device 200 by the tags 417 of the collet 217.

As discussed herein, the obturator 215 can be moved distally, or fixed in a distal position by applying pressure to the actuator 260, or indexing a locking mechanism with the actuator 260. When the obturator 215 is moved to a distal position or a fixed distal position, where the collet 217 is disposed within the flared portion 247 of the lumen 245, the tags 417 of the collet 217 can spread, e.g., spring, outward, such than an opening in the splices 419 of the collet 217 can allow for receiving or deploying the needle 280, e.g., via an opening 510 in the distal end of the elongate barrel 210, where the opening 510 can be continuous with, or part of the lumen 245.

As discussed above with respect to the devices 100 and 200, in some implementations, a furlow insertion device can include a locking mechanism, such as an indexing locking mechanism. An example indexing locking mechanism is illustrated in FIGS. 6A-6B, 7A-7C, 8A-8B and 9A-9C.

Figure 6B:
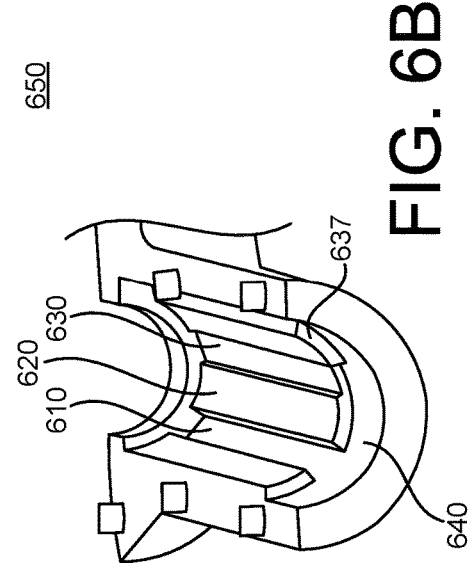
FIGS. 6A and 6B are partial cross-sectional views of housing of a furlow insertion device in which a locking mechanism can be implemented according to an embodiment.
Figure 6A:
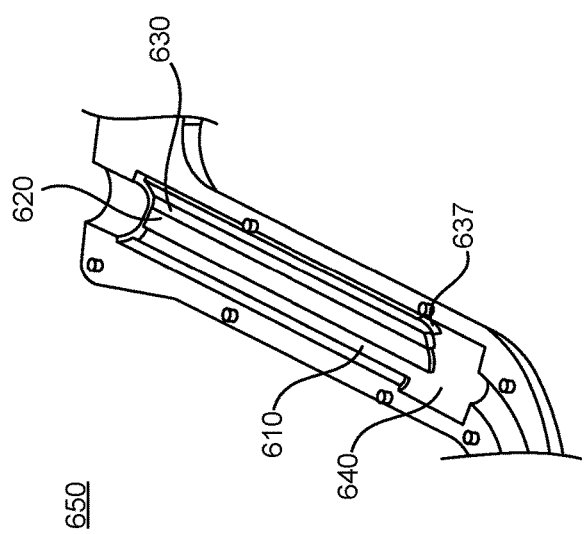

For instance, FIGS. 6A and 6B illustrate a portion of a housing 650 that includes protrusions 620 and grooves 610 and 630 that can be used in implementing a locking mechanism. In some implementations, the protrusions and grooves show in FIGS. 6A and 6B, as well as related elements of the locking mechanism, can be implemented in other portions, or sections of a furlow insertion device, such as in an elongate barrel of a furlow insertion device. For instance, in some implementations the housing 650 (or other housing, such as the housing 250) can include a cylindrical bore therethrough, and a separate cylindrical piece that includes the protrusions and grooves 610 and 630 can be disposed within the cylindrical bore in the housing 650 (or other housing).

Figure 7C:
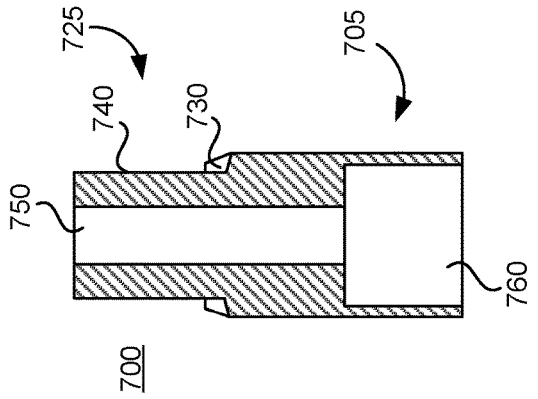
FIG. 7C is a cross-sectional view of the indexer of FIGS. 7A and 7B according to an implementation.
Figure 7B:
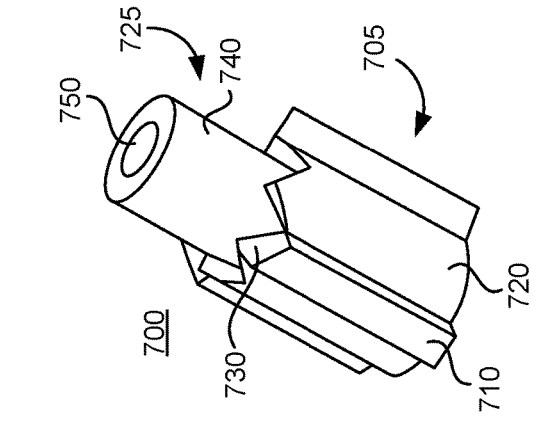
FIGS. 7A and 7B are views of an indexer of a locking mechanism according to an embodiment.
Figure 7A:
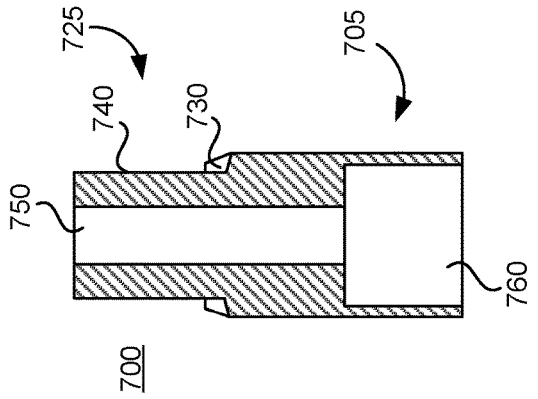
Figure 8A:
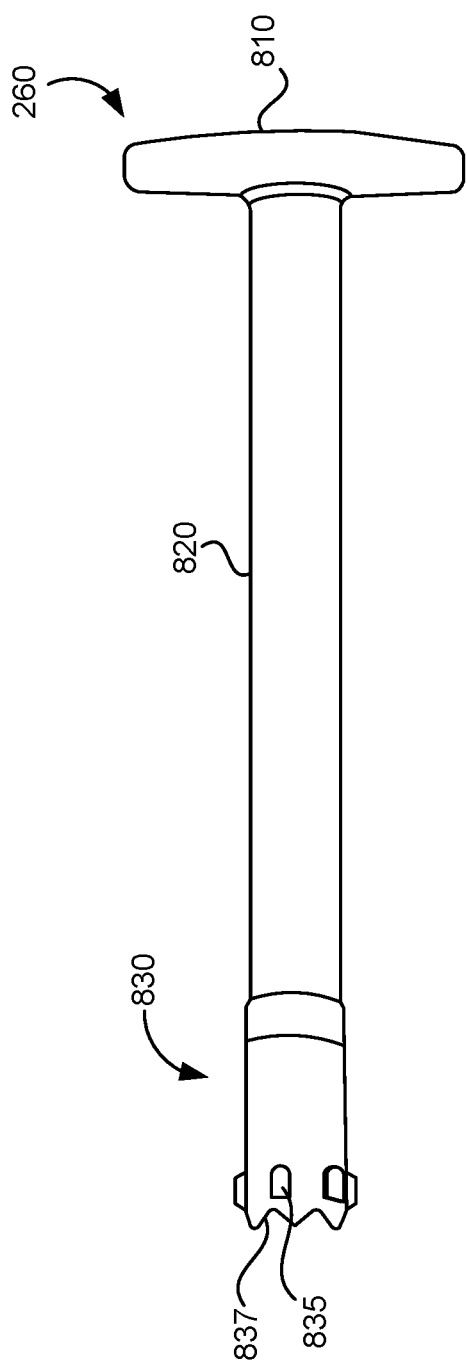
FIG. 8A is a plunger for actuating a furlow insertion device that can operate in conjunction with the indexer of FIGS. 7A-7C in the housing of FIGS. 6A and 6B according to an embodiment.
Figure 8B:
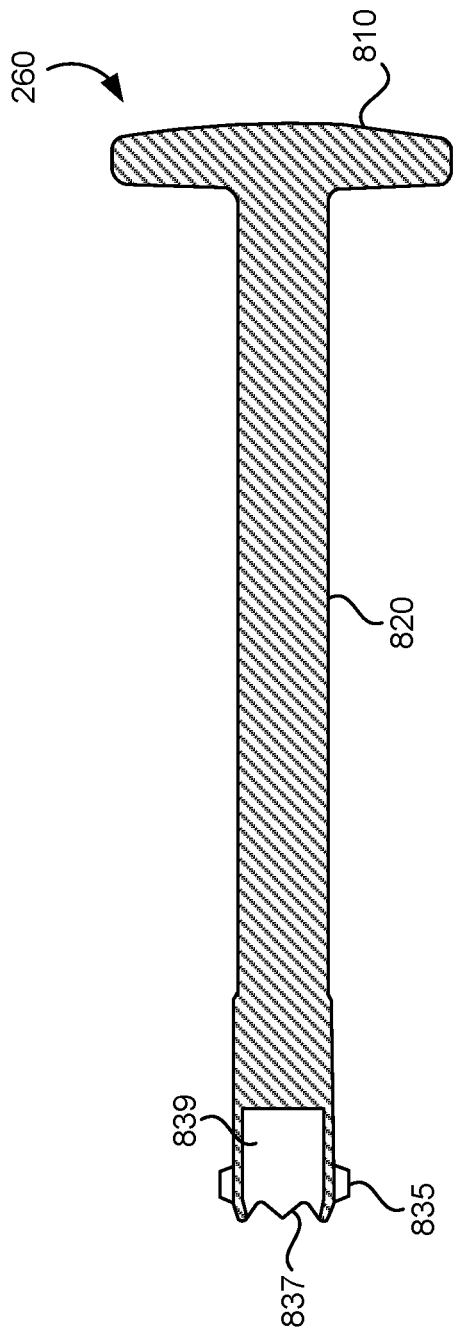
FIG. 8B is a cross-sectional view of the plunger of FIG. 8A according to an embodiment.
Figure 9A:
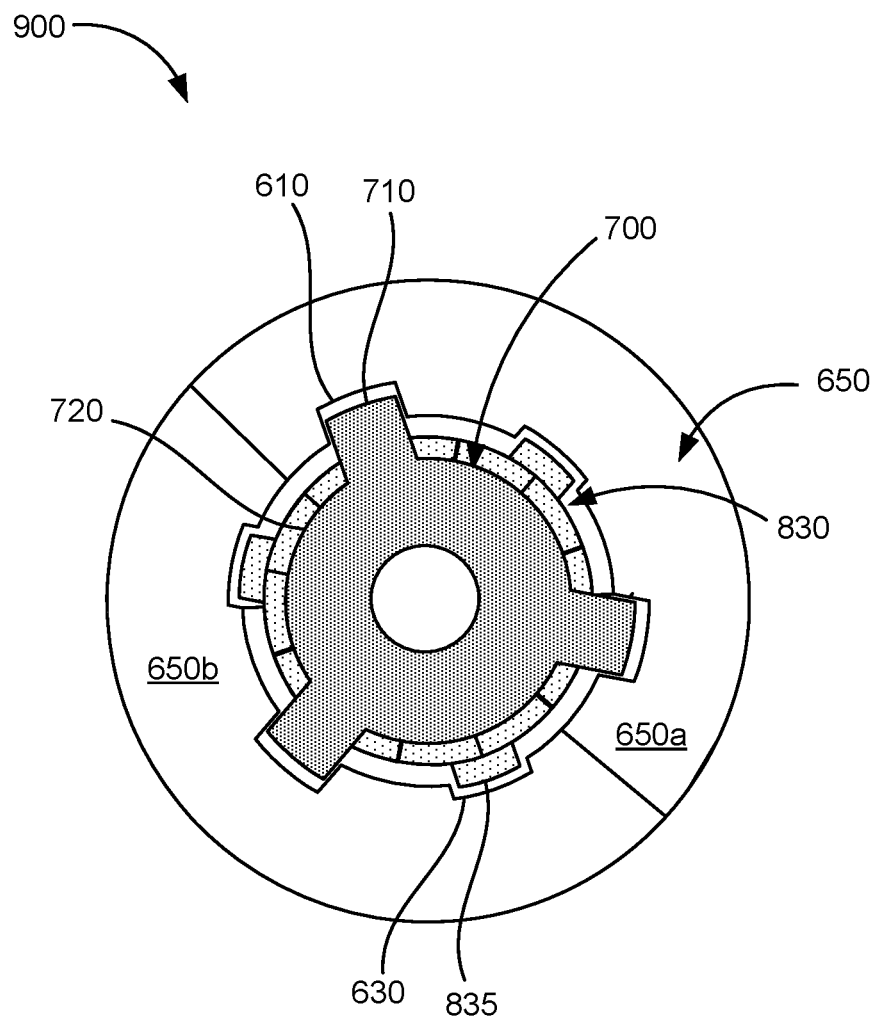
FIGS. 9A, 9B and 9C are diagrams illustrating a locking mechanism according to an embodiment.
Figure 9C:
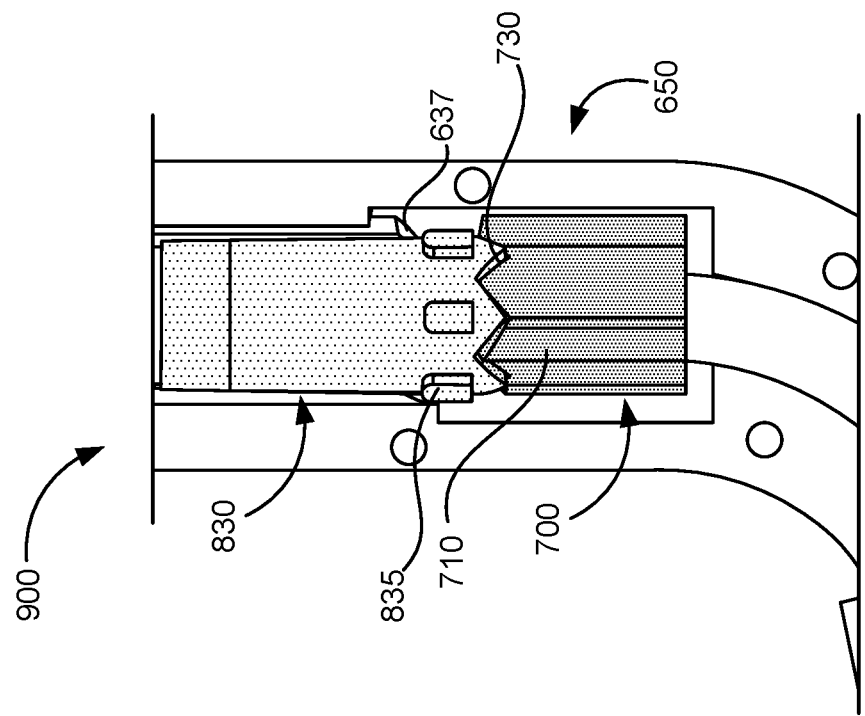
Figure 9B:
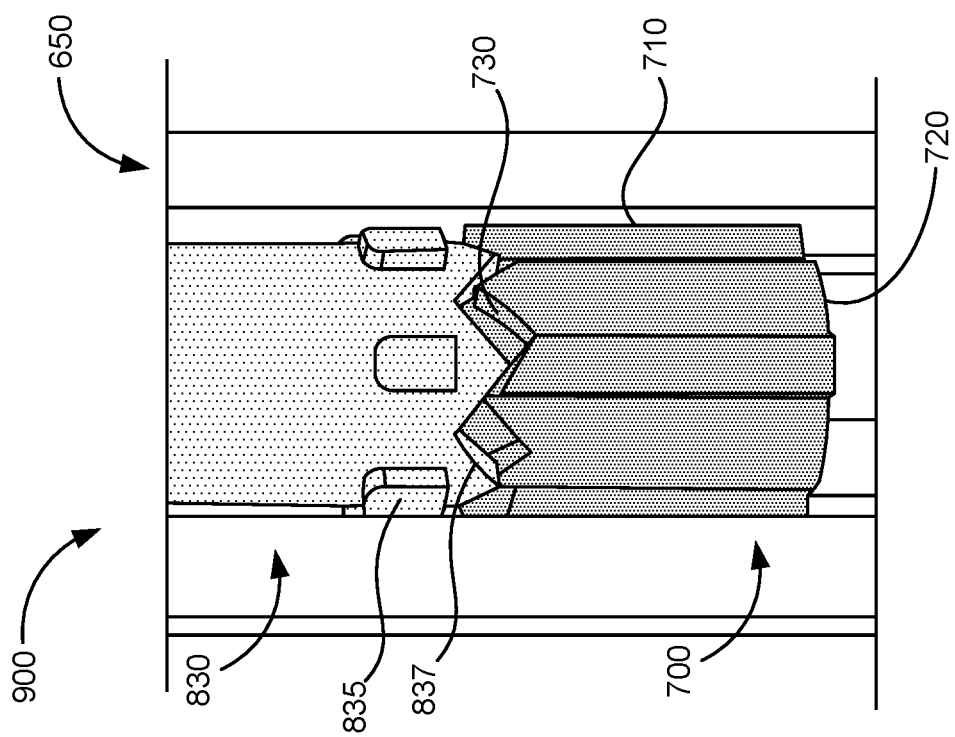

FIGS. 7A-7C illustrate an indexer 700 that can be included in a locking mechanism of a furlow insertion tool, while FIGS. 8A and 8B illustrate an example implementation of the actuator 260 that includes an end portion 830 that can work cooperatively with the indexer 700 in the housing 650 to implement an indexing locking mechanism. Operation of a locking mechanism 900 including the elements of FIGS. 6A-6B, 7A-7C and 8A-8B is illustrated in FIGS. 9A-9C. For purposes of illustration and by way of example, the locking mechanism of FIGS. 6A-6B, 7A-7C, 8A-8B and 9A-9C is described with further reference to FIGS. 1A-1B and 2-5.

Furlow insertion devices, such as the device 200, that include such a locking mechanism can provide for easier loading of, and securing of the needle 280 within the collet 217 of the obturator 215. For example, as discussed above, such a locking mechanism can lock or fix the obturator in a distal position, such that the collet 217 is disposed within the flared portion 247 of the elongate barrel 210's lumen 245. This locking of the obturator in a fixed distal position allows for a user to load the needle 280 in the open tags 417 of the collet 217, without the need to maintain pressure on the actuator 260 of the device, e.g., to prevent the biasing spring 225 from decompressing and moving (biasing) the obturator 215 to a proximal fixed position.

Once the needle 280 is loaded in the tags 417 of the collet 217, the actuator 260 can be depressed again, causing the locking mechanism to index, which can allow the biasing spring 225 to decompress and move, or bias the obturator 215 to a proximal fixed position, e.g., with the collet 217 disposed within the cylindrical portion 249 of the lumen 245 and the tags 417 pressed inward onto the needle 280, such that the needle 280 is retained or held in place in the collet 217 by the tags 417. Accordingly, said in other words, the locking mechanism FIGS. 6A-6B, 7A-7C, 8A-8B and 9A-9C can be activated to lock the obturator 215 in a fixed distal position by depressing the actuator 260 until a mechanical stop (e.g., the indexer 700 reaching an end of a lumen in the housing 650), and then releasing the actuator 260. The locking mechanism can then be deactivated to return the obturator 215 to its biased, fixed proximal position by, again, depressing the actuator 260 until the mechanical stop, and then releasing the actuator 260.

FIGS. 6A and 6B are partial cross-sectional views of the housing 650 of a furlow insertion device in which a locking mechanism can be implemented according to an example embodiment. The views shown in FIGS. 6A and 6B show an inner surface of the housing 650, which can be used in implementing an indexing locking mechanism. Further, the views of FIGS. 6A and 6B are isometric views from two different angles and at two different degrees of magnification, the view of FIG. 6B being enlarged (magnified) and further sectioned, as compared with the view of FIG. 6A.

As shown, in FIGS. 6A and 6B, the housing 650 can include a plurality of protrusions 620 that are radially disposed around the inner surface of the housing 650. The protrusions 620 can define grooves 610 and grooves 630 on the inner surface, where the grooves 610 and 630, and the protrusions 620 can alternate around a circumference of the inner surface of the housing 650, such as in the arrangement shown in FIGS. 6A and 6B, as well as in FIG. 9A. For instance, as is illustrated in FIG. 9A, in some implementations, the inner surface of the housing 650 can include three grooves 610 and three grooves 630, as shown the grooves 610 can alternative with the grooves 630, with protrusions 620 disposed between, the grooves 610 being deeper than the grooves 630. In example implementations, the grooves 610 and 630, and the protrusions 620 are sized, shaped and located so that they can work cooperatively with protrusions and surfaces of the end portion 830 of the actuator 260, and protrusions and surfaces of the indexer 700, to operate as an indexing locking mechanism for device 200 and the obturator 215, using the example of the device 200. For instance, the protrusions 620 can include angled surface 637 that work cooperatively with the indexer 700 to affect indexing of a locking mechanism.

As further shown in FIGS. 6A and 6B, the inner surface of the housing 650 includes an open area 640, without protrusions or grooves. The open area 640, in this example locking mechanism, can allow the indexer 700 to rotate, in cooperation with the actuator 260 and the housing 650, to index the locking mechanism between a first position, with the obturator locked or fixed in a distal position, and a second position, with the obturator locked or fixed in a proximal position, such as is described herein.

FIGS. 7A and 7B are views of an indexer 700 of a locking mechanism according to an embodiment. FIG. 7C is a cross-sectional view of the indexer 700 of FIGS. 7A and 7B according to an embodiment.

FIGS. 7A and 7B are isometric views of the indexer 700 from two different angles, to illustrate different perspectives of the features of the indexer 700. As shown in FIGS. 7A and 7B, the indexer 700 can include two diametric sections 705 and 725, which are cylindrical and axially connected. In some implementations, the sections 705 and 725 of the indexer can be monolithically formed. The section 705 includes a plurality of angled and beveled surfaces 730 that form V-shaped ridges or troughs disposed along an upper circumferential edge of the section 705. As shown in FIGS. 7A and 7B, a depth of each V-shaped trough ends at an outside diameter or surface 740 of the section 725 of the indexer 705.

As also shown in FIGS. 7A and 7B, each alternative apex of the V-shaped troughs of the section 705 has a protrusion 710, where a width of each protrusion 710 extends from an apex of corresponding V-shaped trough and extends vertically along the length of the section 705 of the indexer. In this example, when implemented with the housing 650 in the locking mechanism illustrated in FIGS. 9A-9C, the protrusions 710 of the indexer 700 are configured to slide, or ride within the deeper grooves 610 of the housing 650. The protrusion 710 are sized such that they do not slide (will not enter) the shallower grooves 630 of the housing 650. The protrusions 710 are also sized such that the indexer 700 rotates, or indexes in the open area 640 of the housing, such as when the protrusions 710 are outside the grooves 610 of the housing 650.

The section 705 of the indexer 700 also includes surfaces 720 that form part of the V-shaped troughs of the section 705. The surfaces 720 of the section 705 are defined, in part, by the protrusions 710 of the section 705.

The section 725 of the indexer 700 can be cylindrical with a center bore 750. In some implementations, the center bore 750 can be eliminated. The section 725 includes an outer surface 740. Section 725 can be sized so that the outer surface 740 fits within a bore defined in the end portion 830 of the actuator 260, such as the bore shown below in FIG. 8B, which can coaxially align the indexer 700 with the end portion 830 of the actuator 260. FIG. 7C illustrates a cross-sectional view of the indexer 700, sectioned through a central axis of the indexer 700. As shown in FIG. 7C, the indexer 700 can include a counter-bore 760 in the section 705, where the counter bore 760 can be sized to receive a proximal end of the connecting rod 735, or a proximal end of the obturator, depending on a specific location of the locking mechanism in the device 200.

FIG. 8A is a plunger that can be used to implement the actuator 260 of, for example, the device 200 according to an embodiment. The actuator 260 of FIG. 8A can operate in conjunction with the housing 650 of FIGS. 6A and 6B, and the indexer 700 of FIGS. 7A-7C to implement an indexing locking mechanism in a furlow insertion device, such as in the device 200. FIG. 8B is a cross-sectional view of the actuator (plunger) 260 of FIG. 8A according to an embodiment.

The actuator (plunger) 260 of FIGS. 8A and 8B includes a button 810 that can be used to depress the actuator in the device 200, e.g., to affect distal movement of the obturator 215 and/or to index a locking mechanism, such as the locking mechanism of the present example. The actuator 260, as shown in FIG. 8A, includes a cylindrical section 820 and an end portion 830, where the end portion 830 can operate in cooperation with the housing 650 and the indexer 700 to implement an indexing locking mechanism.

The end portion 830 of the actuator 260 of FIGS. 8A and 8B, as shown in the cross-sectional view of FIG. 8B, can include a counter bore 839 which can receive the section 725 of the indexer 700, so that the indexer 700 and the end portion 830 are concentrically aligned. As shown in FIGS. 8A and 8B, the end portion 830 can include V-shaped protrusions 837 which can operate cooperatively with the V-shapes troughs of the indexer 700 in implementing an indexing locking mechanism. As further illustrated in FIGS. 8A and 8B, the end portion 830 of the actuator 260 can include protrusions 835 that are disposed on its outer surface. In this example, the protrusions 835 of the end portion 835 can be sized to ride in the shallower grooves 620 of the housing 650. For instance, the protrusions 835 can allow the actuator 260 of FIGS. 8A and 8B to move axially along the grooves 620, while preventing the actuator 260 from rotational motion within the housing 650, which could result in changing alignment of the end portion 830 with indexer 700, causing improper operation of the locking mechanism of this example. For instance, the locking mechanism can be configured such that the protrusions 835 do not exit the grooves 620, even when the actuator 260 is fully depressed. The protrusions 835 can be prevent from exiting the grooves 620 due to the indexer 700 contacting a mechanical stop in the housing 650 and preventing axial movement of the protrusions 835 out of the grooves 620 and into the open area 640 of the housing 650.

FIGS. 9A, 9B and 9C are diagrams illustrating a locking mechanism 900 according to an embodiment. The locking mechanism 900, which can also be referred to as an indexing locking mechanism can be implemented, as was indicated above, using the housing 650 of FIGS. 6A and 6B, the indexer 700 of FIGS. 7A-7C and the actuator (plunger) 260 of FIGS. 8A and 8B. Accordingly, in the discussion of FIGS. 9A-9C, further reference is made to FIGS. 6A and 6B, FIGS. 7A-7C, FIGS. 8A and 8B, and the elements of the housing 650, the indexer 700 and the actuator 260 (as illustrated in FIGS. 8A and 8B).

FIG. 9A is a plan view along the section line 9A-9A in FIG. 2, illustrating an example arrangement of the elements of the locking mechanism 900 in the housing 650 (or the housing 250). For instance, FIG. 9A illustrates the axial arrangement of the indexer 700 and the end portion 830 of the actuator 260 of FIGS. 8A and 8B within the housing 650. For purposes of clarity, other elements of the device 200, such as the handle 270, are not shown in FIG. 9A. As shown in FIG. 9A, the housing 650 (or 250) can be of two-piece construction, including a first housing portion 650a and a second housing portion 650b.

As illustrated in FIG. 9A, in the locking mechanism 900, the protrusions 710 can be disposed in, or ride in the deeper grooves 610 of the housing 650. As also shown in FIG. 9A, the protrusions 835 of the end portion 830 can be disposed in, or ride in the shallower grooves 630 of the housing 650. Further, as illustrated in FIG. 9A, the protrusions 620 of the housing 650 are disposed between the grooves 610 and the grooves 630 in an alternating arrangement around a circumference of the inner surface of the housing 650.

FIG. 9B is a side view of the locking mechanism 900 in the arrangement shown in FIG. 9A. That is, FIG. 9B illustrates the indexer 700 with its protrusions 710 riding in the grooves 610 of the housing 650 and the end portion 830 of the actuator 260 with its protrusions 835 riding in the grooves 630. As shown in FIG. 9B, in this arrangement, the V-shaped troughs or protrusions 730 of the indexer 700 are offset from the V-shaped protrusions 837 of the end portion 830. When pressure is applied to the actuator 260 (e.g., when the actuator 260 is depressed) both the end portion 830 of the actuator 260 and the indexer 700 will slide axially (downward in FIG. 9B) within their respective grooves of the housing, where the grooves prevent rotational movement of the indexer 700 and the actuator 260.

As shown in FIG. 9C, once the actuator has been depressed to move the protrusions 710 of the indexer 700 out of the grooves 610 of the housing 650, and into the open area 640 of the housing, pressure applied to the actuator 260 and counter-pressure from the biasing spring 225 can cause the V-shaped protrusions 730 of the indexer to align with the V-shaped protrusions 837 of the end portion 830, as shown in FIG. 9C. This alignment of the indexer 700 and the end portion 830 of the actuator 260 will affect a slight rotational motion of the indexer 700. When pressure is removed from the actuator 260, the biasing force of the spring 225 will push both the indexer 700 and the actuator 260 distally (upward) in the housing 635.

As the indexer 700 rises in response to force from the biasing spring 225, peaks of its V-shaped protrusions 730 will ride along the angled edges 637 of the protrusions 620 in the housing 650, which will cause further rotational motion of the indexer 700, and align the protrusion 710 of the indexer 700 with either the grooves 610 or the grooves 630 of the housing 650. The rotational motion of the indexer 700 resulting from depressing and releasing of the actuator 260 can be referred to as indexing of the locking mechanism 900. If the protrusions 710, after indexing of the locking mechanism 900, are aligned with the deeper grooves 610, the protrusions 710 of the indexer 700 will ride in the grooves 610 and an obturator, such as the obturator 215 will be biased to its proximal position. If, however, the protrusions 710, after indexing of the locking mechanism 900, are aligned with the shallower grooves 630, the protrusions 710 of the indexer 700 will be prevented from rising by the shallower grooves 620, the biasing spring 625 will remain compressed, and the obturator of the associated insertion device will be locked, or fixed in its distal position.

Figure 10A:
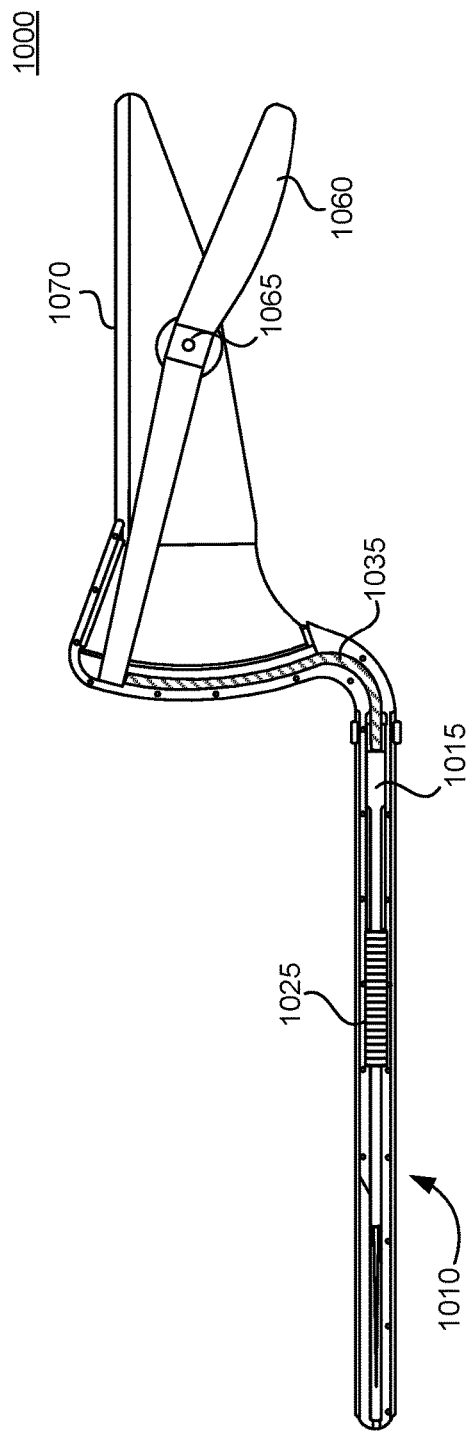
FIGS. 10A and 10B are cross-sectional views of another furlow insertion device according to an embodiment.
Figure 10B:
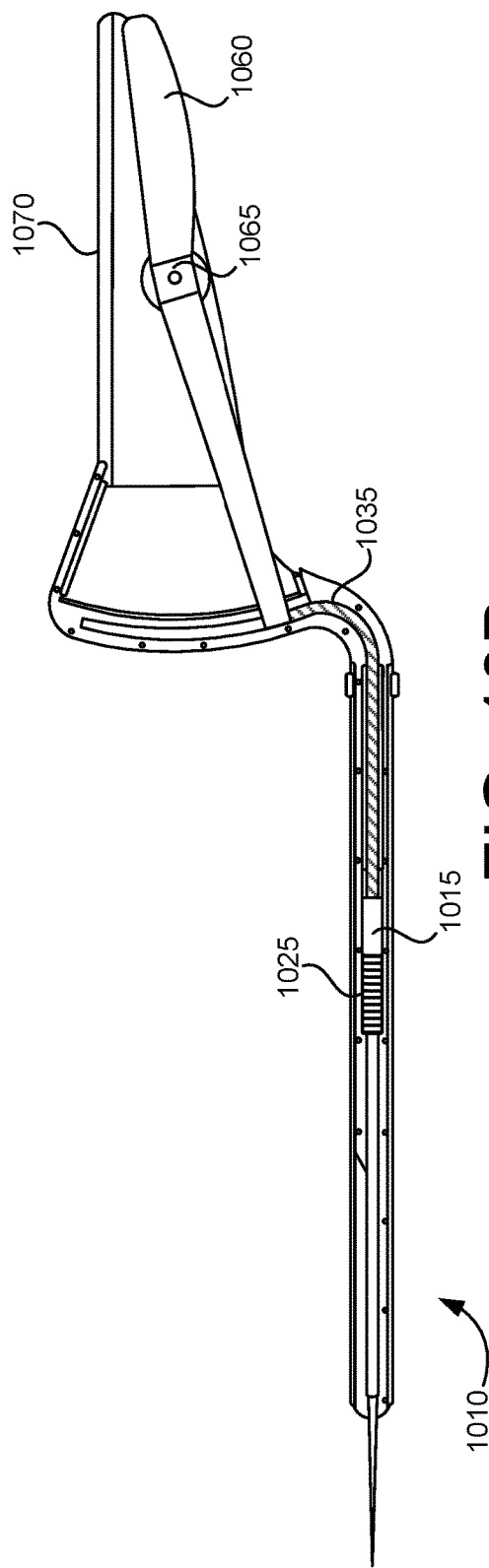

FIGS. 10A and 10B are cross-sectional views of another furlow insertion device 1000 according to an embodiment. As shown in FIGS. 10A and 10B, the device 1000 includes an elongate barrel 1010 that is similar in configuration to the elongate barrel 210 of the device 200. Accordingly, for purposes of brevity, at least some aspects and features of the elongate barrel 1010 are not described in detail with respect to FIGS. 10A and 10B.

As illustrated in FIGS. 10A and 10B, the device 1000 includes a squeeze handle actuator 1060 that rotates on a pivot (e.g., a pin, an axle, etc.) 1065. The pivot 1065 and the actuator 1060 can be affixed to, or coupled with a handle 1070 of the device 1000. The device 1000 is shown in FIG. 10A with an obturator 1015 in a proximal position. For instance, pressure is not being applied to the actuator 1060. Accordingly, the biasing spring 1025 can maintain the obturator 1015 in a fixed, proximal position. In the proximal position of FIG. 10A, a collet of the obturator 1015 can be compressed, so as to retain a needle within the collet and within the elongate barrel 1010.

In FIG. 10B, the device 1000 is illustrated with the obturator 1015 in a distal position. For instance, in the arrangement shown in FIG. 10B, pressure may be applied to the actuator 1060, so as to apply a force to a connecting rod 1035 to affect distal movement of the obturator 1015, e.g., to the distal position for loading or deployment of a needle. In certain implementations, if the device 1000 includes a locking mechanism, the obturator 1015, as shown in FIG. 10B, can be locked, or fixed in its distal position.

FIGS. 11A and 11B are cross-sectional views of another furlow insertion device 1100 according to an embodiment. As shown in FIGS. 11A and 11B, the device 1100 includes an elongate barrel 1110 that is similar in configuration to the elongate barrel 210 of the device 200. Accordingly, for purposes of brevity, at least some aspects and features of the elongate barrel 1110 are not described in detail with respect to FIGS. 11A and 11B.

As illustrated in FIGS. 11A and 11B, the device 1100 includes a rotating knob actuator 1160 that rotates within a housing 1150. The actuator 1160 includes a tab 1165 that contacts a connecting rod 1135. As shown in FIGS. 11A and 11B, the device 1100 can also include a handle 1170 that is coupled with the housing 1150.

In FIG. 11A, the device 1100 is illustrated with an obturator 1115 in a proximal position. For instance, pressure is not being applied to the actuator 1160. Accordingly, the biasing spring 1125 can maintain the obturator 1115 in a fixed, proximal position. In the proximal position of FIG. 11A, a collet of the obturator 1115 can be compressed, so as to retain a needle within the collet and within the elongate barrel 1110.

In FIG. 11B, the device 1100 is illustrated with the obturator 1115 in a distal position. For instance, in the arrangement shown in FIG. 11B, pressure may be applied to the actuator 1160, so as to apply a force to the connecting rod 1135, via the tab 1165, to affect distal movement of the obturator 1115, e.g., to a distal position for loading or deployment of a needle. In certain implementations, as shown in FIG. 11B, the obturator 1115 of the device 1100 can be locked, or fixed in its distal position by the locking mechanism 900, such as described above with respect to FIGS. 9A-9C.

FIG. 12 is a flowchart of a method 1200 for inserting a penile prosthesis according to an embodiment. For instance, a cylindrical (e.g., inflatable, malleable, etc.) penile prosthesis can be implanted (inserted, etc.) in a corpus cavernosum of a patient in accordance with the method 1200. Further, the method 1200 can be implemented using the insertion devices described herein. For purposes of illustration, and by way of example, the method 1200 of FIG. 12 is described with further reference to the insertion devices 100 and 200 of FIGS. 1A-1C, 2, 3, 4 and 5, and the locking mechanism 900 of FIGS. 6, 7, 8 and 9, as appropriate. Reference is further made to FIG. 1D in the discussion of FIG. 12. It is understood that, in some implementations, other insertion tools can be used to perform the method 1200. Also, in some implementations, the order of the operations of the method 1200 can vary, additional operations can be added and/or operations shown in FIG. 12 can be omitted, depending on the particular implementation.

As shown in FIG. 12, at block 1210, the method 1200 can include making a penoscrotal or an infrapubic incision in a body of a patient, wherein the incision is located such that a corpus cavernosum of the patient's penis is accessible through the incision. At block 1220, the method 1200 includes manipulating the insertion device 200, via the handle 270, to perform a first insertion of the elongate barrel 210 of the insertion device 200 into the corpus cavernosum, the insertion of the elongate barrel 210 being made via the incision of block 1210.

At block 1230, the method 1200 can include sliding the measurement ring 230 along the elongate barrel 210, such that the measurement ring 230 is proximate (adjacent to, touching, in contact with, etc.) the incision. The measurement ring 230 can be slid along the groove or slot 240 in the elongate barrel 210. At block 1240, the method 120 can include extracting (withdrawing, removing, etc.) the elongate barrel 210 from the patient (e.g., removing the elongate barrel 210 from the corpus cavernosum via the incision). Also at block 1240, the method 1200 can include reading (determining, etc.) an insertion depth of the elongate barrel 210 in the corpus cavernosum, where the insertion depth is determined based on the measurement scale 220 on the elongate barrel 210 and a position of the measurement ring 230 on the elongate barrel 210 (and the measurement scale 220).

At block 1250, an appropriate penile prosthesis, such as the prosthesis 190, can be selected based on the insertion depth measurement of block 1240. Also at block 1250, the selected prosthesis can be attached (coupled with, affixed to, etc.) the suture 185. At block 1260 the suture of block 1250 can be threaded into (inserted through) an eye of a needle, such as the Keith needle 280.

At block 1270, the method 1200 can include capturing a needle (e.g., the Keith needle 280) within the elongate barrel 210 of the insertion device 200, such as within the tags 417 of the collet 217. For instance, capturing the needle 280 in the tags 417 of the collet 217 can include locking the obturator 215 in its distal position, such as by using a locking mechanism (e.g., the locking mechanism 900) that can be included in the insertion device 200. As described herein, when the obturator 215 is in its distal position, the tags 417 of the collet 217 can be biased within the flared portion 247 of the lumen 245 such that the tags are spaced (open, etc.) to receive the needle 280. The needle 280 can then be captured within the elongate barrel 210 by indexing the locking mechanism 900. For instance, the locking mechanism 900 can be indexed by actuating the insertion device 200, causing the biasing spring 225 to bias the obturator 215 to its proximal position, resulting in the tags 417 of the collet 217 being compressed within the cylindrical portion 249 of the lumen 245, and capturing (grabbing, retaining, holding, etc.) the needle 290 in the collet 217 and within the elongate barrel 210. Also at block 1270, the method 1200 can include pulling (guiding, etc.) a suture (e.g., the suture 185) that is inserted (threaded, etc.) in an eye of the needle 280 along (into, etc.) the slot 240 in the elongate barre 210.

At block 1280, the method 1200 can include performing a second insertion of the elongate barrel 210 into the corpus cavernosum of the patient via the incision. At block 1290, the insertion tool 200 can be actuated (e.g., to lock the obturator in its distal position), causing the needle 280 to, at least partially, exit the patient's body via a glans of the patient's penis. Also at block 1290, the elongate barrel 210 can again be removed (withdrawn, etc.) from the corpus cavernosum of the patient, leaving the needle 280 and the suture 185 in place (e.g., with the needle 280 partially extending out of the glans and the suture 185 extending from an eye of the needle 280 within the corpus cavernosum to the penile prosthesis being implanted). At block 1295, the penile prosthesis can be implanted into the corpus cavernosum of the patient by drawing the prosthesis through the incision and into to the corpus cavernosum by pulling the needle 280 and the suture 185 through (out of, etc.) the glans of the patient's penis. After completing implantation of the penile prosthesis in accordance with the method 1200, the insertion tool 200 can be disposed of (e.g. as medical waste).

While certain features of the described implementations have been illustrated as described herein, many modifications, substitutions, changes and equivalents will now occur to those skilled in the art. It is, therefore, to be understood that the appended claims are intended to cover all such modifications and changes as fall within the scope of the embodiments.

What is claimed is:

1. An insertion device comprising:
    an elongate barrel aligned along a first longitudinal axis, a distal end of the elongate barrel having an opening defined therein;
    a lumen defined within the elongate barrel, the lumen being accessible through the opening;
    a housing disposed at a proximal end of the elongate barrel, the housing including an elbow portion coupled with the elongate barrel and a straight portion coupled with the elbow portion, the straight portion being aligned along a second longitudinal axis, the second longitudinal axis defining an angle with the first longitudinal axis; and
    an obturator disposed within the lumen of the elongate barrel, the obturator being movable within the lumen between a proximal position in the elongate barrel and a distal position in the elongate barrel,
    the obturator, in its distal position in the elongate barrel, is configured to receive a needle via the opening, and
    the obturator, in its proximal position in the elongate barrel, is configured to secure the needle within the elongate barrel.

2. The insertion device of claim 1, wherein the obturator includes a collet disposed at a distal end of the obturator, the collet having a plurality of tags,
    the plurality of tags being biased to receive the needle when the obturator is in its distal position in the elongate barrel, and
    the plurality of tags being compressed to secure the needle when the obturator is in its proximal position in the elongate barrel.

3. The insertion device of claim 2, wherein the lumen of the elongate barrel includes:
    a flared portion disposed at the distal end of the elongate barrel, the flared portion being configured to allow the plurality of tags to bias to receive the needle when the collet is disposed within the flared portion; and
    a cylindrical portion disposed proximal to the flared portion, the cylindrical portion being configured to compress the plurality of tags when the collet is disposed within the cylindrical portion.

4. The insertion device of claim 3, wherein a diameter of the flared portion of the lumen is greater than a diameter of the cylindrical portion of the lumen.

5. The insertion device of claim 1, further comprising:
    a biasing spring axially disposed around at least a portion of the obturator and disposed within the lumen of the elongate barrel, the biasing spring being configured to bias the obturator in its proximal position.

6. The insertion device of claim 1, further comprising:
    a measurement scale disposed on an exterior surface of the elongate barrel; and
    a measurement ring that is slidable along the elongate barrel to indicate an insertion depth of the elongate barrel.

7. The insertion device of claim 6, wherein the elongate barrel includes a groove or a slot defined therein, the groove or slot extending along the elongate barrel, the measurement ring being slidable along the groove or the slot.

8. The insertion device of claim 6, wherein the measurement scale is inscribed on an exterior surface of the elongate barrel.

9. The insertion device of claim 1, wherein the angle is between ninety degrees and one-hundred-eighty degrees, the housing has a lumen disposed therethrough, further comprising:
    an actuator disposed at a distal end of the housing;
    a flexible connecting rod having a first portion disposed within the lumen of the housing and a second portion disposed within the lumen of the elongate barrel, the flexible connecting rod being disposed between the actuator and the obturator, the actuator and the flexible connecting rod being configured, in response to movement of the actuator by a user, to move the obturator from its proximal position to its distal position.

10. The insertion device of claim 9, further comprising:
    a handle coupled with the housing, the handle being aligned along a third longitudinal axis.

11. The insertion device of claim 10, wherein the third longitudinal axis is parallel with the first longitudinal axis.

12. The insertion device of claim 1, further comprising:
    a housing disposed at a proximal end of the elongate barrel and coupled with the elongate barrel, the housing having a lumen disposed therethrough;
    an actuator disposed at a distal end of the housing;
    a connecting rod having a first portion disposed within the lumen of the housing and a second portion disposed with the lumen of the elongate barrel, the connecting rod being disposed between the actuator and the obturator, the actuator and the connecting rod being configured, in response to movement of the actuator by a user, to move the obturator from its proximal position to its distal position.

13. The insertion device of claim 12, wherein the connecting rod is a flexible connecting rod.

14. The insertion device of claim 12, wherein the actuator includes at least one of:
    a plunger;
    a squeeze lever; or
    a rotating knob disposed in the housing.

15. The insertion device of claim 1, further comprising a locking mechanism that is configured to selectively lock the obturator in its distal position.

16. The insertion device of claim 1, further comprising an indexing mechanism configured to, in response to actuation of the insertion device, alternate between a first fixed position and a second fixed position, wherein:
when the indexing mechanism is in its first fixed position, the obturator is fixed in its distal position in the elongate barrel, and
when the indexing mechanism is in its second fixed position, the obturator is fixed in its proximal position in the elongate barrel.

17. A method for inserting a penile prosthesis, the method comprising:
making a penoscrotal or an infrapubic incision in a body of a patient;
capturing a needle in an obturator of an insertion device to secure the needle within an elongate barrel of the insertion device the elongate barrel includes a groove or a slot defined therein, the groove or slot extending along the elongate barrel, a ring being slidable along the groove or the slot;
pulling a suture inserted in an eye of the needle into a slot in the elongate barrel;
using a handle of an insertion device, manipulating the insertion device to perform an insertion of the elongate barrel, via the incision, into a corpus cavernosum of a penis of the patient;
attaching a penile prosthesis to the suture;
actuating the insertion device to deploy at least a portion of the needle through a glans of the penis;
withdrawing the elongate barrel from the corpus cavernosum and the incision;
implanting the penile prosthesis in the corpus cavernosum by pulling the prosthesis through the incision and into to the corpus cavernosum by pulling the needle and suture through the glans.

18. The method of claim 17, wherein capturing the needle in the obturator includes capturing the needle with tags of a collet disposed at a distal end of the obturator.

19. The method of claim 17, wherein the insertion is a second insertion, the method further comprising, prior to performing the second insertion:
using the handle of the insertion device, manipulating the insertion device to, via the incision, perform a first insertion of the elongate barrel into the corpus cavernosum;
sliding the ring disposed on the barrel proximate the incision;
withdrawing the elongate barrel from the corpus cavernosum and the incision; and
determining, based on a measurement scale inscribed on the elongate barrel and position of the ring on the elongate barrel, a depth of insertion of the elongate barrel in the corpus cavernosum;
the penile prosthesis being selected based on the depth of insertion.

20. The method of claim 19, wherein sliding the ring includes sliding the ring along a groove or slot in the elongate barrel.

* * * * *